US00PP11671P

United States Patent [19]

Van Hee

[11] Patent Number: Plant 11,671

[45] Date of Patent: Dec. 5, 2000

[54] DAHLIA PLANT NAMED 'DAPADRED'

[75] Inventor: François Van Hee, Enkhuizen, Netherlands

[73] Assignee: Ball Floraplant, a division of Ball Horticultural Co., West Chicago, Ill.

[21] Appl. No.: 09/328,633

[22] Filed: Jun. 9, 1999

[51] Int. Cl.[7] ..... A01H 5/00

[52] U.S. Cl. ..... Plt./321

[58] Field of Search ..... Plt./321

*Primary Examiner*—Bruce R. Campell
*Assistant Examiner*—Kent L. Bell
*Attorney, Agent, or Firm*—C. A. Whealy

[57] ABSTRACT

A distinct cultivar of Dahlia plant named 'Dapadred', characterized by its fully double dark red purple inflorescences; uniform growth habit; dark green foliage; and strong peduncles that hold inflorescences above the foliage.

1 Drawing Sheet

BACKGROUND OF THE INVENTION

The present invention relates to a new and distinct variety of Dahlia plant, botanically known as *Dahlia variabilis*, and hereinafter referred to by the name 'Dapadred'.

The new Dahlia is a product of a planned breeding program conducted by the Inventor in Enkhuizen, The Netherlands. The objective of the breeding program was to create new compact Dahlia cultivars suitable for potted plant production.

The new Dahlia originated from a cross made by the Inventor of two proprietary *Dahlia variabilis* selections identified as code number 015 as the female, or seed, parent and DRED as the male, or pollen, parent. The cultivar 'Dapadred' was discovered and selected by the Inventor as a flowering plant within the progeny of the stated cross in a controlled environment in Enkhuizen, The Netherlands, in 1992.

Asexual reproduction of the new Dahlia by terminal cuttings harvested in Enkhuizen, The Netherlands, has shown that the unique features of this new Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dapadred'. These characteristics in combination distinguish 'Dapadred' as a new and distinct cultivar:

1. Fully double dark red purple inflorescences.
2. Dark green foliage.
3. Strong peduncles that hold inflorescences above the foliage.

The new Dahlia is somewhat similar in ray floret color to the Dahlia cultivar 'Lizzy', disclosed in U.S. Plant Pat. No. 9,846. However in side-by-side comparisons conducted in West Chicago, Ill., plants of the new Dahlia differ from plants of the cultivar 'Lizzy' in the following characteristics:

1. Plants of the new Dahlia are more vigorous, taller and broader than plants of the cultivar 'Lizzy'.
2. Plants of the new Dahlia have larger and darker green leaves than plants of the cultivar 'Lizzy'.

3. Ray florets of plants of the new Dahlia are slightly darker in color than plants of the cultivar 'Lizzy'.
4. Plants of the new Dahlia have longer peduncles than plants of the cultivar 'Lizzy'.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a side perspective view of a typical plant of the new Dahlia. Ray floret and foliage colors may appear different from the actual colors due to light reflectance.

DETAILED BOTANICAL DESCRIPTION

The following observations and measurements describe plants grown in West Chicago, Ill., in 10-cm containers in a glass greenhouse with average day temperatures about 20 to 22° C., average night temperatures about 18 to 20° C., and light levels about 2,500 to 3,000 foot-candles. Plants were planted about 4 weeks after propagating unrooted cuttings and were pinched about three weeks after planting. Plants were in full flower and descriptions were taken about 8 weeks after planting.

In the following description, color references are made to The Royal Horticultural Society Colour Chart except where general terms of ordinary dictionary significance are used.

Botanical classification: *Dahlia variabilis* 'Dapadred'.

Parentage:

*Female, or seed, parent.*—Proprietary *Dahlia variabilis* selection identified as code number 015, not patented.

*Male, or pollen, parent.*—Proprietary *Dahlia variabilis* selection identified as code name DRED, not patented.

Propagation:

*Type.*—By terminal cuttings.

*Time to initiate roots.*—About 4 days with temperatures of 22° C.

*Time to develop roots.*—About 14 days with temperatures of 22° C.

*Rooting habit.*—Terminal cuttings propagate easily, roots fibrous, thick and well-branched.

*Tubers.*—Plants of the new Dahlia will form tubers under short day conditions, that is at least 13 to 14 hours of darkness.

Plant description:

*Appearance.*—Pot plant and perennial garden plant. Upright and mounded, uniform growth habit, rounded apex. Very vigorous. Appropriate for 10 to 12.5-cm containers. Plants typically flower about 8 weeks after planting rooted cuttings.

*Plant height.*—About 24 cm.

*Plant spread.*—About 24.5 cm.

*Stem description.*—Quantity: About six per plant. Basally branching, however, plants typically require pinching to enhance lateral branch development. Lateral branch length: About 13 cm. Lateral branch diameter: About 5.5 mm. Internode length: About 3.25 cm. Texture: Smooth. Color: 144B.

*Foliage description*—Arrangement: Young foliage, leaves single; fully expanded foliage, leaves compound, trifoliate; opposite. Quantity of leaves per lateral branch: About 11. Leaf length: About 11.25 cm. Leaf width: About 12 cm. Terminal leaflet length: About 6.5 cm. Terminal leaflet width: About 4 cm. Leaflet shape: Ovate. Leaflet apex: Acuminate. Leaflet base: Attenuate. Leaflet margin: Serrate to dentate. Petiole length: About 6 cm. Petiole diameter: About 3 mm. Color: Young foliage, upper surface: 141A. Young foliage, lower surface: 141A. Fully expanded foliage, upper surface: 147A. Fully expanded foliage, lower surface: 191A. Petiole: 144B.

Flowering description:

*Appearance.*—Fully double inflorescence form. Inflorescences hemispherical and borne on terminals above foliage, arising from leaf axils on strong peduncles; inflorescences face upright and/or outward. Typically about one inflorescence per lateral stem; about 10 to 15 inflorescences and buds per plant. Disc and ray florets arranged acropetally on a capitulum. Persistent. Not fragrant.

*Flowering response.*—Under natural conditions, plants flower intermittently from July to October in the Northern Hemisphere.

*Flower longevity.*—Flowers last about one to two weeks on the plant dependent on temperature.

*Flower bud* (*just before opening*).—Shape: Spherical. Length: About 1.75 cm. Diameter: About 2.25 cm. Color: Light green.

*Inflorescence size.*—Diameter: About 8.5 cm. Depth (height): About 5 cm. Disc diameter: About 7.5 mm.

*Ray florets.*—Quantity per inflorescnece: About 75. Shape: Elliptic. Length: About 3.5 cm. Width: About 2.4 cm. Apex: Cuspidate. Base: Attenuate. Margin: Entire. Texture: Smooth, dull. Color: When opening, upper surface: 187A. When opening, lower surface: 187B. Fully opened, upper surface: Darker than 59A, color does not fade. Fully opened, lower surface: 59B.

*Disc florets.*—Elongated, cylindrical; shiny. Quantity: About 31. Length: About 1.3 cm. Diameter: About 2 mm. Color: Between 21A and 23A.

*Peduncle.*—Aspect: Erect and strong. Length: About 8 cm. Texture: Smooth. Color: 144B with dark purple, 183C, streaks.

*Involucral bracts.*—Quantity: About 8. Diameter of bract whorl: About 4.5 cm. Shape: Elliptic. Tip: Acute. Margin: Entire. Texture: Smooth, shiny. Color, upper and lower surfaces: 137B.

*Reproductive organs.*—Androecium (Present on disc florets): Anther size: About 2.5 mm. Anther color: 1B. Pollen color: 13A. Gynoecium (Present on ray and disc florets): Stigma color: 2B. Ovary color: 145B.

Seed production: Seed production has not been observed.

Disease resistance: Resistance to known Dahlia diseases has not been observed on plants grown under commercial greenhouse conditions.

It is claimed:

1. A new and distinct cultivar of Dahlia plant named 'Dapadred', as illustrated and described.

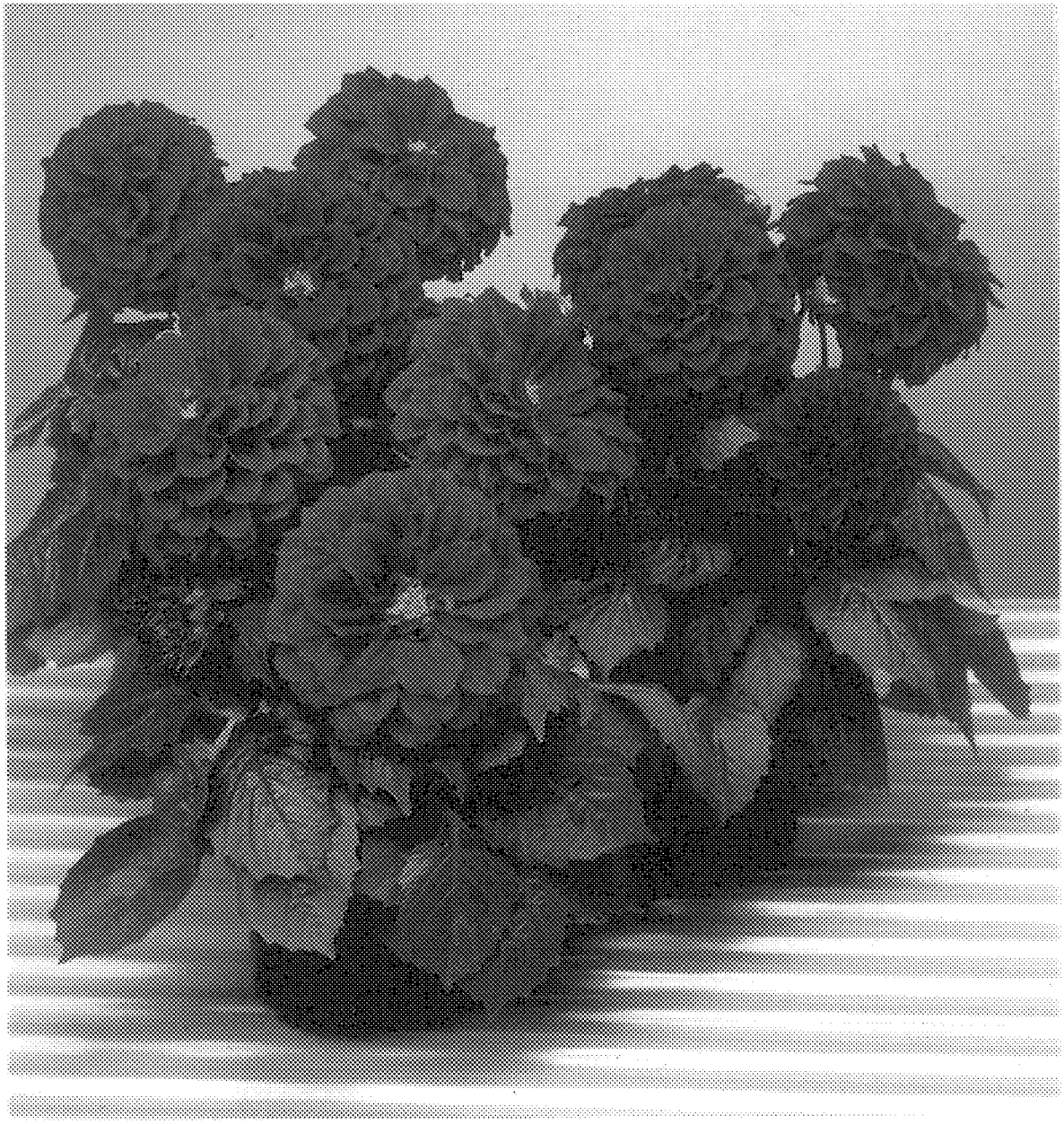

* * * * *